United States Patent
Öztürk et al.

(10) Patent No.: US 11,389,560 B2
(45) Date of Patent: Jul. 19, 2022

(54) ELECTRICAL CONDUCTIVE SURGICAL SUTURE PRODUCTION METHOD

(71) Applicant: ISTANBUL TEKNIK ÜNIVERSITESI, Istanbul (TR)

(72) Inventors: Yetkín Öztürk, Istanbul (TR); Esra Alveroğlu Durucu, Istanbul (TR)

(73) Assignee: ISTANBUL TEKNIK UNIVERSITESI, Istanbul (TR)

(*) Notice: Subject to any disclaimer, the term of this patent is extended or adjusted under 35 U.S.C. 154(b) by 1072 days.

(21) Appl. No.: 16/061,657

(22) PCT Filed: Nov. 28, 2017

(86) PCT No.: PCT/TR2017/050605
§ 371 (c)(1),
(2) Date: Jun. 13, 2018

(87) PCT Pub. No.: WO2018/125012
PCT Pub. Date: Jul. 5, 2018

(65) Prior Publication Data
US 2020/0197561 A1    Jun. 25, 2020

(30) Foreign Application Priority Data
Dec. 28, 2016 (TR) ................. 2016/19867

(51) Int. Cl.
| | |
|---|---|
| *A61L 17/14* | (2006.01) |
| *A61B 17/06* | (2006.01) |
| *A61L 17/10* | (2006.01) |
| *A61L 17/12* | (2006.01) |
| *A61B 17/00* | (2006.01) |

(52) U.S. Cl.
CPC ...... *A61L 17/145* (2013.01); *A61B 17/06166* (2013.01); *A61L 17/10* (2013.01); *A61L 17/105* (2013.01); *A61L 17/12* (2013.01); *A61B 2017/00526* (2013.01); *A61L 2420/02* (2013.01)

(58) Field of Classification Search
CPC .... C08J 5/00; A61F 2/02; C12N 11/14; A61L 17/145
See application file for complete search history.

(56) References Cited

U.S. PATENT DOCUMENTS

| | | | | |
|---|---|---|---|---|
| 8,329,205 | B2 * | 12/2012 | Hadba | A61P 31/00 424/426 |
| 2005/0107872 | A1 | 5/2005 | Mensah et al. | |
| 2008/0003251 | A1 * | 1/2008 | Zhou | A61F 2/82 424/423 |
| 2008/0103525 | A1 | 5/2008 | Shalaby | |
| 2016/0215108 | A1 * | 7/2016 | Webster | A01N 25/08 |

FOREIGN PATENT DOCUMENTS

| | | |
|---|---|---|
| CN | 104958780 A | 10/2015 |
| EP | 2075012 A1 | 7/2009 |
| WO | 02076288 A2 | 10/2002 |

OTHER PUBLICATIONS

Laleh Ghasemi-Mobarakeh et al., Application of conductive polymers, scaffolds and electrical stimulation for nerve tissue engineering, Journal of tissue engineering and regenerative medicine, Jan. 10, 2011, pp. e17-e35, vol. 5. No. 4.

\* cited by examiner

*Primary Examiner* — Dah-Wei D. Yuan
*Assistant Examiner* — Andrew J Bowman
(74) *Attorney, Agent, or Firm* — Bayramoglu Law Offices LLC

(57) ABSTRACT

This invention is related to a surgical suture production method that has been given electrical conductivity to the surgical suture. The surgical suture production method subjected to the invention comprises the steps of, dissolving a conductive or semi conductive polymer that is to be used as coating material in a solvent together with a dopant that increases electrical conductivity, immersing the surgical suture inside this solution and coating the suture, taking the suture out of the solution and obtaining an electrical conductive layer on the suture after the solution on it has evaporated.

18 Claims, No Drawings

ELECTRICAL CONDUCTIVE SURGICAL SUTURE PRODUCTION METHOD

CROSS REFERENCE TO RELATED APPLICATIONS

This application is the national phase entry of International Application PCT/TR2017/050605, filed on Nov. 28, 2017 which is based upon and claims priority to Turkish Patent Application No. 2016/19867, filed on Dec. 28, 2016 the entire contents of which are incorporated herein by reference.

TECHNICAL FIELD

This invention is related to a surgical suture producing method which has been gained electrical conductivity property to the surgical suture.

The invention is particularly related to a surgical suture producing method, that shall be used in suturing the nerves which are ruptured in injuries.

BACKGROUND

Surgical sutures is one of the increasingly developing materials among other materials used for suturing wounds in the medical market. Staples, bandages and other wound closure materials have never been used as a common material in surgeries.

Surgical sutures have been used by surgeons since 4000 years. Medical scripts from 2000 B.C. comprise information that wires and nerves were used in order to tie and stitch wounds. In several ancient cultures interesting methods have been tried in order to suture wounds. As an example, the Greeks have used horsetail hair threaded onto needle eye made from bone As far as it is known from a papyrus, mostly linen surgical sutures were used in order to suture the edges of the wounds and before that materials based on collagen and organic fibers were used, moreover dried intestines, dried tendons, horse hair, strips from animal skin, women's hair, and fibers from tree barks were also used.

Surgical suture materials that have been used until 1930's have generally been catgut silk, low amounts of linen and wool. Synthetic fibers have started to be used with nylon since World War II in 1941. Following this, polyesters, polyacrylonitriles, polyolefins, have been used with low or high success rates. The characteristic of this period is that the fibers used during surgical operations were popular. In other words, at that time any material that was specifically aimed to be used in a surgical procedure was designed or developed. Many surgical suture materials that were present in the market having several physical and biological characteristics were first created in the textile market and then they have been continued to be used in surgical purposes.

Today as signals received from the brain are not transmitted by the suture during the healing process of nerve cells, the degree and duration of healing only differs according to the condition of the wound and the regeneration parameter of the nerve cells that have been sutured end-to-end. A need to bring novelties to surgical sutures has risen in order to provide a solution to shorten this differing healing process and to increase the regeneration capacity of nerve cells.

In the known state of the art by the Chinese patent document that was filed on Jun. 30, 2015 and numbered CN104958780, a production method for a surgical suture having bacteriostatic and high drawing abilities has been described.

It has been foreseen that by giving electricity conducting abilities to such surgical sutures that are being used in the sector, nerve healing percentages can be increased. For this reason, a need for developing a production method of a surgical suture that can conduct electricity and at the same time that is bio-compatibility has risen.

SUMMARY

The aim of this invention is to provide a production method of a surgical suture that has been given electrical conductive properties.

The surgical suture production method subject to the invention comprises the following steps;
dissolving a conductive or semi conductive polymer that is to be used as coating material in a solvent together with a dopant that increases conductivity,
coating the suture by immersing it inside this solution,
taking the suture out of the solution,
after evaporating the solvent, electrical conductive layer on the suture is obtained.

DETAILED DESCRIPTION

The surgical sutures that are available in the market and that are used in suturing nerves have been coated to have a fine layer on the suture by using biocompatible conductive materials. Said surgical suture can be produced from materials such as polyglactin 910, polyglycolic acid, glycolic polymer, lactic polymer, polyglyconate, polyglecapron 25, glycomer 631, polyglytone 6211, silk, polyester, polyamide, polypropylene, polybutester, polymerized caprolactam or stainless steel.

As coating materials, Poly(3-hexylthiophene-2,5-diyl), polyacetylene, poliphenylene vinyl, polypyrrole and derivatives thereof, polythiophene and derivatives thereof, polyaniline and derivatives thereof, polyphenylene sulphate, polyfluorene and derivatives thereof, polyphenylene and derivatives thereof, polycarbazole and derivatives thereof, poly(3,4-ethylenedioxythiophene), poly(carbazole-dithiophene-benzothiadiazole) or Poly[2,1,3-benzothiadiazole-4,7-diil[4,4-bis(2-ethylhexyl)-4H-cyclopenta[2,1-b: 3,4-b']dithiophene-2,6-Diil]] can be used.

Dodecylbenzene sulfonic acid, iodine, bromide, camphor sulphonic acid or 2,3,5,6-Tetrafluoro-7,7,8,8-tetracyanoquinodimethane can be used as conductivity increasing dopant.

As a solution p-Xylene, m-cresol, dioxane or dimethyl sulfoxide can be used.

The production method of the surgical suture subjected to the invention comprises the steps of;
dissolving a conductive or semi conductive polymer that is to be used as a coating material in a solvent together with a dopant that increases the electrical conductivity,
immersing the surgical suture inside this solution and coating it,
taking the suture out of the solution,
obtaining a conductive layer on the suture after the solution is evaporated.

What is claimed is:
1. A surgical suture production method comprising:
obtaining a solution by dissolving an electrically conductive or semi electrical conductive polymer in a solvent together with a dopant, wherein the polymer is used as a coating material and the dopant increases the electri- cal conductivity, and wherein the dopant is at least one agent selected from a group consisting of dodecylbenzene sulfonic acid, bromide, camphor sulphonic acid, and 2,3,5,6-Tetrafluoro-7,7,8,8-tetracyanoquinodimethane;

coating a surgical suture by:
immersing the surgical suture inside the solution;
taking the surgical suture out of the solution; and
obtaining a conductive layer on the surgical suture after the solution on the surgical suture has evaporated.

2. The surgical suture production method according to claim 1, wherein the surgical suture is produced from any material selected from a group consisting of polyglactin 910, polyglycolic acid, glycolic polymer, lactic polymer, polyglyconate, poliglecaprone 25, glycomer 631, polyglytone 6211, silk, polyester, polyamide, polypropylene, polybutester, polymerized caprolactam, and stainless steel.

3. The surgical suture production method according to claim 2, wherein the coating material is at least one material selected from a group consisting of Poly(3-hexylthiophene-2,5-diyl), polyacetylene, polyphenylene vinyl, polypyrrole, polythiophene, polyaniline, polyphenylene sulphate, polyfluorene, polyphenylene, polycarbazole, poly(3,4-ethylenedioxythiophene), poly(carbazole-dithiophene-benzothiadiazole), and Poly[2,1,3-benzothiadiazole-4,7-diil [4,4-bis (2-ethylhexyl)-4H-cyclopenta [2,1-b: 3,4-b'] dithiophene-2,6-Diol]].

4. The surgical suture production method according to claim 3, wherein the solution comprises any agent selected from a group consisting of p-Xylene, m-cresol, dioxane, and dimethyl sulfoxide.

5. The surgical suture production method according to claim 2, wherein the coating material is at least one material selected from a group consisting of Poly(3-hexylthiophene-2,5-diyl), polyacetylene, polyphenylene vinyl, polythiophene, polyaniline, polyphenylene sulphate, polyfluorene, polyphenylene, polycarbazole, poly(3,4-ethylenedioxythiophene), poly(carbazole-dithiophene-benzothiadiazole), and Poly[2,1,3-benzothiadiazole-4,7-diil [4,4-bis (2-ethylhexyl)-4H-cyclopenta [2,1-b: 3,4-b'] dithiophene-2,6-Diol]].

6. The surgical suture production method according to claim 2, wherein the coating material is at least one material selected from a group consisting of Poly(3-hexylthiophene-2,5-diyl), poly(3,4-ethylenedioxythiophene), poly(carbazole-dithiophene-benzothiadiazole), and Poly[2,1,3-benzothiadiazole-4,7-diil [4,4-bis (2-ethylhexyl)-4H-cyclopenta [2,1-b: 3,4-b'] dithiophene-2,6-Diol]].

7. The surgical suture production method according to claim 3, wherein the solution comprises p-Xylene.

8. The surgical suture production method according to claim 3, wherein the solution comprises m-cresol.

9. The surgical suture production method according to claim 3, wherein the solution comprises dioxane.

10. The surgical suture production method according to claim 3, wherein the solution comprises dimethyl sulfoxide.

11. A surgical suture production method comprising:
obtaining a solution by dissolving an electrically conductive or semi electrical conductive polymer in a solvent together with a dopant, wherein the polymer is used as a coating material and the dopant increases the electrical conductivity, and wherein the dopant is at least one agent selected from a group consisting of dodecylbenzene sulfonic acid, camphor sulphonic acid, and 2,3,5,6-Tetrafluoro-7,7,8,8-tetracyanoquinodimethane;

coating a surgical suture by:
immersing the surgical suture inside the solution;
taking the surgical suture out of the solution; and
obtaining a conductive layer on the surgical suture after the solution on the surgical suture has evaporated.

12. The surgical suture production method according to claim 11, wherein the surgical suture is produced from any material selected from a group consisting of polyglactin 910, polyglycolic acid, glycolic polymer, lactic polymer, polyglyconate, poliglecaprone 25, glycomer 631, polyglytone 6211, silk, polyester, polyamide, polypropylene, polybutester, polymerized caprolactam, and stainless steel.

13. The surgical suture production method according to claim 12, wherein the coating material is at least one material selected from a group consisting of Poly(3-hexylthiophene-2,5-diyl), polyacetylene, polyphenylene vinyl, polypyrrole, polythiophene, polyaniline, polyphenylene sulphate, polyfluorene, polyphenylene, polycarbazole, poly(3,4-ethylenedioxythiophene), poly(carbazole-dithiophene-benzothiadiazole), and Poly[2,1,3-benzothiadiazole-4,7-diil [4,4-bis (2-ethylhexyl)-4H-cyclopenta [2,1-b: 3,4-b'] dithiophene-2,6-Diol]].

14. The surgical suture production method according to claim 13, wherein the solution comprises any agent selected from a group consisting of p-Xylene, m-cresol, dioxane, and dimethyl sulfoxide.

15. A surgical suture production method comprising:
obtaining a solution by dissolving an electrically conductive or semi electrical conductive polymer in a solvent together with a dopant, wherein the polymer is used as a coating material and the dopant increases the electrical conductivity, and wherein the dopant is 2,3,5,6-Tetrafluoro-7,7,8,8-tetracyanoquinodimethane;

coating a surgical suture by:
immersing the surgical suture inside the solution;
taking the surgical suture out of the solution; and
obtaining a conductive layer on the surgical suture after the solution on the surgical suture has evaporated.

16. The surgical suture production method according to claim 15, wherein the surgical suture is produced from any material selected from a group consisting of polyglactin 910, polyglycolic acid, glycolic polymer, lactic polymer, polyglyconate, poliglecaprone 25, glycomer 631, polyglytone 6211, silk, polyester, polyamide, polypropylene, polybutester, polymerized caprolactam, and stainless steel.

17. The surgical suture production method according to claim 16, wherein the coating material is at least one material selected from a group consisting of Poly(3-hexylthiophene-2,5-diyl), polyacetylene, polyphenylene vinyl, polypyrrole, polythiophene, polyaniline, polyphenylene sulphate, polyfluorene, polyphenylene, polycarbazole, poly(3,4-ethylenedioxythiophene), poly(carbazole-dithiophene-benzothiadiazole), and Poly[2,1,3-benzothiadiazole-4,7-diil [4,4-bis (2-ethylhexyl)-4H-cyclopenta [2,1-b: 3,4-b'] dithiophene-2,6-Diol]].

18. The surgical suture production method according to claim 17, wherein the solution comprises any agent selected from a group consisting of p-Xylene, m-cresol, dioxane, and dimethyl sulfoxide.

* * * * *